United States Patent [19]

Sprunt et al.

[11] Patent Number: 4,924,187

[45] Date of Patent: May 8, 1990

[54] METHOD FOR MEASURING ELECTRICAL ANISOTROPHY OF A CORE SAMPLE FROM A SUBTERRANEAN FORMATION

[75] Inventors: Eve S. Sprunt, Farmers Branch; R. Michael Davis, Bedford; W. David Kennedy, Dallas; Samuel H. Collins, De Soto, all of Tex.

[73] Assignee: Mobil Oil Corporation, New York, N.Y.

[21] Appl. No.: 364,281

[22] Filed: Jun. 12, 1989

[51] Int. Cl.$^5$ ............................................. G01V 3/02
[52] U.S. Cl. ................................................. 324/376
[58] Field of Search ....................... 324/376, 377, 323; 73/153

[56] References Cited

U.S. PATENT DOCUMENTS

| | | |
|---|---|---|
| 3,302,101 | 1/1967 | Glanville ............................ 324/376 |
| 3,839,899 | 10/1974 | McMillen . | 
| 3,982,177 | 9/1976 | Walker et al. ....................... 324/376 |
| 4,379,407 | 4/1983 | Masse et al. . |
| 4,380,930 | 4/1983 | Podhvasky et al. . |
| 4,467,642 | 8/1984 | Givens . |
| 4,486,714 | 12/1984 | Davis, Jr. et al. .................. 324/376 |
| 4,543,821 | 10/1985 | Davis, Jr. ......................... 324/376 X |
| 4,546,318 | 10/1985 | Bowden . |
| 4,628,267 | 12/1986 | Lee et al. .............................. 324/376 |
| 4,644,283 | 2/1987 | Vinegar et al. ...................... 324/376 |
| 4,646,000 | 2/1987 | Wills ................................ 324/376 X |
| 4,686,477 | 8/1987 | Givens et al. . |
| 4,688,238 | 8/1987 | Sprunt et al. . |

FOREIGN PATENT DOCUMENTS 510561  3/1955  Canada ................................ 324/376

*Primary Examiner*—Reinhard J. Eisenzopf
*Assistant Examiner*—Warren S. Edmonds
*Attorney, Agent, or Firm*—Alexander J. McKillop; Charles J. Speciale; George W. Hager, Jr.

[57] ABSTRACT

A core sample from a subterranean formation is shaped to provide a plurality of parallel, planar outer surfaces. Electrical resistivity is measured in each of the azimuthal directions through the core sample which are perpendicular to each of the pairs of parallel, planar outer surfaces for each of a plurality of differing fluid saturations within the core sample. A logarithmic plot is made of measured resistivity versus water saturation for each of the azimuthal directions through the core sample for which resistivity was measured. If the same logarithmic plot is obtained for all measured azimuthal directions, the core sample is identified as being electrically isotropic. If different logarithmic plots are obtained for at least 2 azimuthal directions the core sample is identified as being electrically anisotropic.

16 Claims, 3 Drawing Sheets

METHOD FOR MEASURING ELECTRICAL ANISOTROPHY OF A CORE SAMPLE FROM A SUBTERRANEAN FORMATION

BACKGROUND OF THE INVENTION

This invention relates to the area of oil and natural gas exploration and, more particularly, to a method for identifying regions of rock formations from which hydrocarbons may be produced.

Hydrocarbon saturation $S_o$ is generally determined from a measured water saturation $S_w$ as follows:

$$S_o = 1 - S_w \tag{1}$$

Water saturation present in a subterranean formation is typically determined from interpretation of conventional electrical (i.e., resistivity) logs taken through a borehole drilled through the formation. Water saturation of the available pore space of the formation is determined from the resistivity log measurements using the Archie equation set forth in "The Electrical Resistivity Log As An Aid In Determining Some Reservoir Characteristics", Trans. AIME, Vol. 46, pp. 54–62, 1942, by G. E. Archie. This equation is expressed as follows:

$$S_w^n = R_w / \phi^m R_t \tag{2}$$

Where "$S_w$" is the fractional water saturation (i.e. free and bound water of the formation expressed as a percent of the available pore space of the formation), "$R_w$" is the formation water resistivity, "$\phi$" is the formation porosity, "$R_t$" is the formation electrical resistivity, "n" is the saturation exponent and "m" is the porosity or cementation exponent. The Archie equation may be expressed in other ways and there are numerous methods in the art for determining, measuring or otherwise obtaining the various components needed to predict fractional water saturation $S_w$ from the formation resistivity, $R_t$, using the equation in any of its forms.

Archie defined two quantities that provided the basis for his water saturation equation (1). The first quantity is the formation factor F which defines the effect of the rock matrix on the resistivity of water as follows:

$$F = R_o / R_w \tag{3}$$

where
$R_o$ = resistivity of water saturated rock and
$R_w$ = water resistivity.

Archie reasoned that for a given value of $R_w$, the formation factor F would decrease with increasing porosity, $\phi$, to some exponent m:

$$F = 1/\phi^m \tag{4}$$

This porosity exponent m has also become known as the Archie cementation exponent. Thus Archie provided a useful characterization of a rock fully saturated with a conducting brine in terms of the water resistivity $R_w$, porosity $\phi$ and a rock parameter m. It is important to note that Archie assumed all conductance to be in the brine.

The second quantity is the resistivity index I defined as the ratio of the resistivity of a rock partially saturated with water and hydrocarbon, $R_t$, to the same rock saturated fully with water, $R_o$, as follows:

$$I = R_t / R_o \tag{5}$$

Archie reasoned that as the water saturation decreased (i.e. hydrocarbon saturation increased) the resistivity $R_t$ and hence I would increase to some exponent n:

$$I = 1/S_w^n \tag{6}$$

where $S_w$ = volume of water in pores/total pore volume. This exponent n has become known as the Archie saturation exponent. It is again important to note that Archie assumed all conductance to be in the brine and further that all pores within the rock have the same water saturation $S_w$.

It is these two equations (4) and (6) for the formation factor F and resistivity index I respectively that Archie combined to provide the water saturation expression $S_w$ of equation (2). Certain logs have provided formation resistivity $R_t$ and porosity $\phi$. Water samples provide the best values for $R_w$. Standard practice is to measure rock sample resistivities $R_o$ and $R_t$ for a number of water saturations and to plot the logarithm of I versus the logarithm of $S_w$. Archie's equations assume such a logarithmic plot is a straight line with slope of $-n$.

Many core samples are, however, not homogenous and electrically isotropic. For such core samples, the Archie saturation exponent n will be strongly dependent on the direction the resistivity measurement is made. For example, a saturation exponent measured across permeability barriers within a core sample may be one and a half times as large as if it were measured parallel to the permeability barriers. This difference can have a large detrimental effect on the determination of hydrocarbon reserves derived from the calculated water saturation of equation (2). It is, therefore, an object of the present invention to determine if a core sample is electrically anisotropic and if the degree of anisotropy changes as the brine saturation of the core sample changes so that an accurate water saturation can be calculated from equation (2).

SUMMARY OF THE INVENTION

The present invention is directed to a method for measuring electrical anisotropy of a core sample from a subterranean formation.

A core sample is shaped to provide a plurality of pairs of parallel, planar outer surfaces. Electrical resistivity is measured in each of the azimuthal directions through the core sample which are perpendicular to each of the pairs of parallel planar outer surfaces for each of a plurality of differing fluid saturations within the core sample. The measured resistivities are compared to identify any electrical anisotropy through the core sample.

In a more specific aspect, an initial fluid saturation is established within the core sample. Electrical resistivity is measured in each of the azimuthal directions through the core sample which are perpendicular to the pairs of parallel, planar outer surfaces at the initial fluid saturation. Fluid saturation is then altered a plurality of times and the electrical resistivity measurements repeated for each differing fluid saturation. A logarithmic plot is made of resistivity versus water saturation for each of the azimuthal directions for which resistivity measurements were carried out. The core sample is identified as being electrically isotropic if the same resistivity is measured in 3 mutually perpendicular directions at all fluid saturations.

In a still more specific aspect, the fluid saturation is repeatedly altered so that the core sample is uniformly desaturated on opposite sides of any permeability barrier within the core sample. This altering of fluid saturation is effected by moving the fluid within the core sample in a direction generally parallel to any permeability barrier as opposed to across any such permeability barrier.

In a yet further aspect, the core sample is shaped to provide three pairs of parallel, planar outer surfaces which are mutually perpendicular to one another, such as a cube for example.

In a still further aspect, the core sample is shaped to provide at least one pair of parallel, planar outer surfaces that is perpendicular to any laminations or permeability barriers within the core sample and at least one pair of parallel, planar outer surfaces that is parallel to any such laminations or permeability barriers. Preferably the core sample is shaped to provide at least two pairs of parallel, planar outer surfaces that are perpendicular to any such laminations or permeability barriers while being mutually perpendicular to on another.

BRIEF DESCRIPTION OF PREFERRED EMBODIMENT

Figure 1:
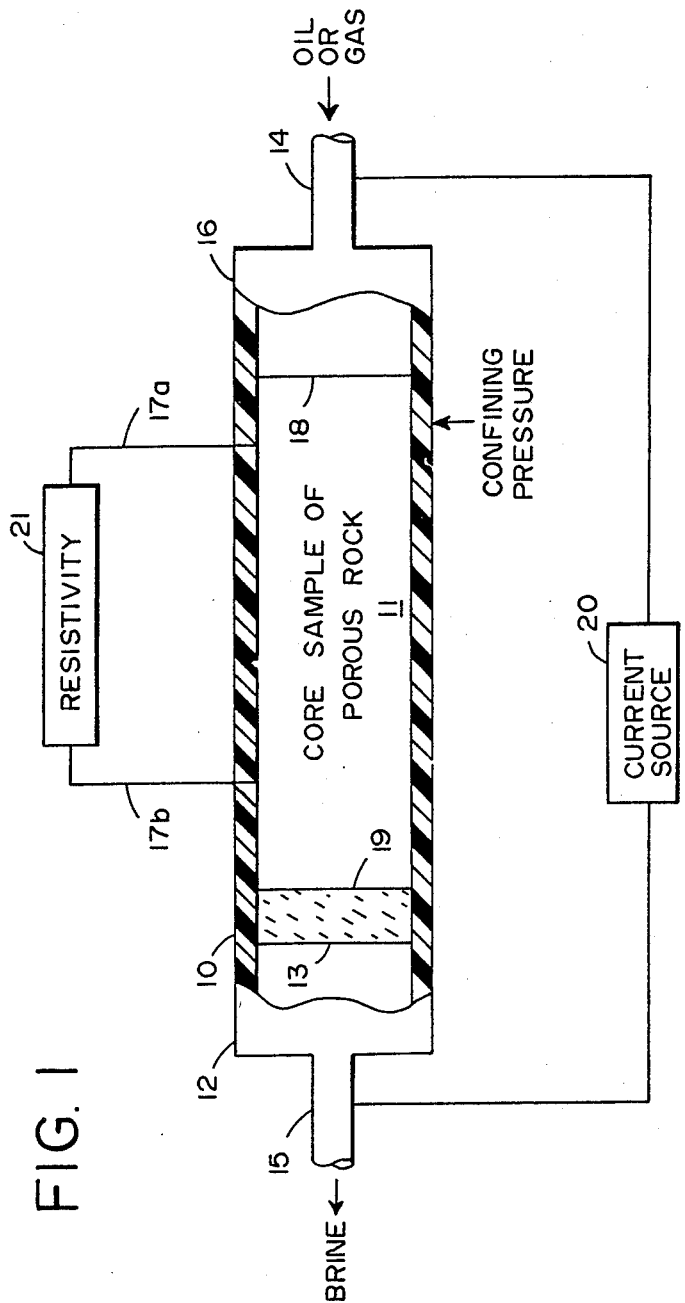
FIG. 1 illustrates apparatus for carrying out resistivity measurements on core samples at varying fluid saturations.

As shown in FIG. 1, a pressure sleeve 10, preferably natural or synthetic rubber surrounds a cylindrical core sample 11 of a porous rock to be measured for resistivity at a plurality of fluid saturations. Positioned between the core sample 11 and end 12 of the pressure sleeve 10 is a porous member 13, which is permeable to a first fluid saturating the core sample, but is impermeable to a second fluid used to displace the first fluid from the core sample. The second, or displacing fluid, is immiscible with the first fluid saturating the core sample and is of different electrical conductivity. This first saturation fluid is the wetting fluid for the porous member 13, which by way of example, may be a ceramic plate or a membrane. Sleeve 10 is placed inside a suitable pressure vessel (not shown) that can be pressurized up to several thousand pounds per square inch. Typical of such pressure vessels are those described in U.S. Pat. Nos. 3,839,899 to McMillan; 4,688,238 to Sprunt et al; and 4,379,407 to Masse et al., the teachings of which are incorporated herein by reference. Through such a pressure vessel a pressure is applied to the sleeve 10 and hence to the porous rock 11. A fluid inlet 14 and a fluid outlet 15 feed into the ends 16 and 12 respectively of the sleeve 10. Both inlet 14 and outlet 15 also serve as current conducting electrodes for passing current from a source 20 through the porous rock 11 when it contains a sufficient amount of electrically conducting fluid. A pair of voltage electrodes 17a and 17b penetrate sleeve 10 and make a contact with the porous rock at spaced locations along the length of the porous rock.

The core sample of porous rock 11 is initially fully saturated, by way of example, with an electrically conducting fluid, such as salt water, preferably brine, and placed under confining pressure. A current is passed through the porous rock and a voltage along the length of the porous rock is measured between electrodes 17a and 17b. Such voltage measurements may be carried out in accordance with the teachings of U.S. Pat. No. 4,467,642 to Givens; U.S. Pat. No. 4,546,318 to Bowden and U.S. Pat. No. 4,686,477 to Givens et al, the teachings of which are incorporated herein by reference. From this voltage the resistance of the porous rock along its length between electrodes 17a and 17b is determined using Ohm's Law by the resistivity unit 21. The resistivity unit 21 calculates resistivity using the measured resistance, the length and the cross-sectional area of the core. A nonconducting fluid displacing liquid such as a hydrocarbon, preferably oil, may the be forced through inlet 14 into end 18 of porous rock 11 to change the fluid saturation condition prior to the making of the next resistivity measurement.

Having now described a typical resistivity measurement carried out in a single direction along the axial direction of a cylindrical core sample as shown in FIG. 1, the present invention of determining electrical anisotropy of a core sample by measuring and comparing resistivity measurements in a plurality of azimuthal directions through the core sample for differing fluid saturations will now be described.

In carrying out the present invention, the first step is the shaping of the core sample to provide for a plurality of pairs of parallel, planar outer surfaces. One example is the shaping of the core sample into a cube wherein each of the three pairs of parallel, planar outer surfaces are mutually perpendicular to one another. For such a cube, resistivity measurements between the parallel surfaces of each pair will likewise have azimuthal directions that are mutually perpendicular so that any electrical anisotropy with azimuthal direction can be identified from a comparison of such measurements. If the same resistivity is measured in 3 mutually perpendicular azimuthal directions at all saturations, then the core sample is electrically isotropic. However, if different resistivities are measured in one or more azimuthal directions, then the core sample is determined to be electrically anisotropic.

More particularly, it has been found that the logarithmic plots of resistivity versus saturation for measurements obtained parallel and perpendicular to any contrasting layers within the core sample such as permeability barriers, diverge for decreasing conducting fluid saturations (see FIG. 4), such permeability barriers are formed by composite layering of materials within the core sample, hereinafter termed "laminations". The Archie saturation exponent measured across any such laminations will be significantly different than such saturation exponent measured parallel to the laminations. Consequently, by measuring resistivity in a plurality of azimuthal directions through a core sample, any electrical anisotropy will be identified.

Figure 2:
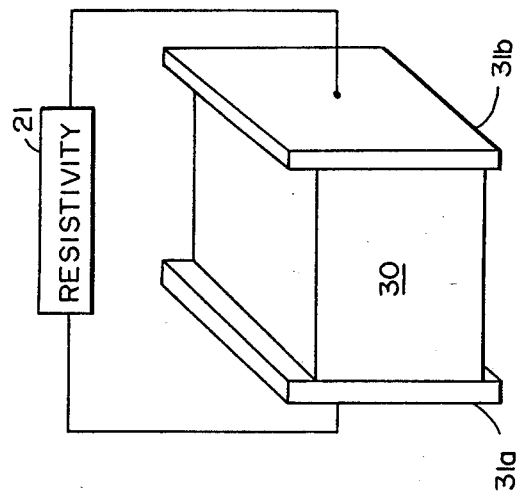
FIG. 2 illustrates apparatus in accordance with the present invention for measuring electrical anisotropy of core samples.

In carrying out the electrical anisotropy measurements in accordance with the present invention it is preferable to utilize measuring electrodes that contact the entire surfaces of each pair of parallel, planar outer surfaces as contrasted to the point or line electrodes utilized in the example of FIG. 1 so that any geometric effects are minimized. An example is illustrated in FIG. 2 where a core sample 30 is shaped as a cube with a first pair of parallel, planar outer surfaces in contact with a pair of plate-type electrodes 31a and 31b. The core sample is initially saturated to a desired fluid saturation condition and a first voltage measurement from across the core sample in a first azimuthal direction is applied to the resistivity unit 21 for calculating core sample electrical resistance for the amount of current passing through the core sample. After this first voltage measurement, the core sample is rotated so that a second of the pair of parallel, planar outer surfaces are in contact with electrodes 31a and 31b and the voltage measurement repeated. After this second voltage measurement, the core sample is again rotated so that the third pair of parallel, planar outer surfaces are in contact with electrodes 31a and 31b and the voltage measurement repeated. These three voltage measurements are used to calculate core sample electrical resistivity at the initial fluid saturation condition of the core sample. Thereafter the fluid saturation is altered a plurality of times with the core sample resistivities being again calculated for each of the three mutually perpendicular azimuthal directions through the core sample.

Figure 4:
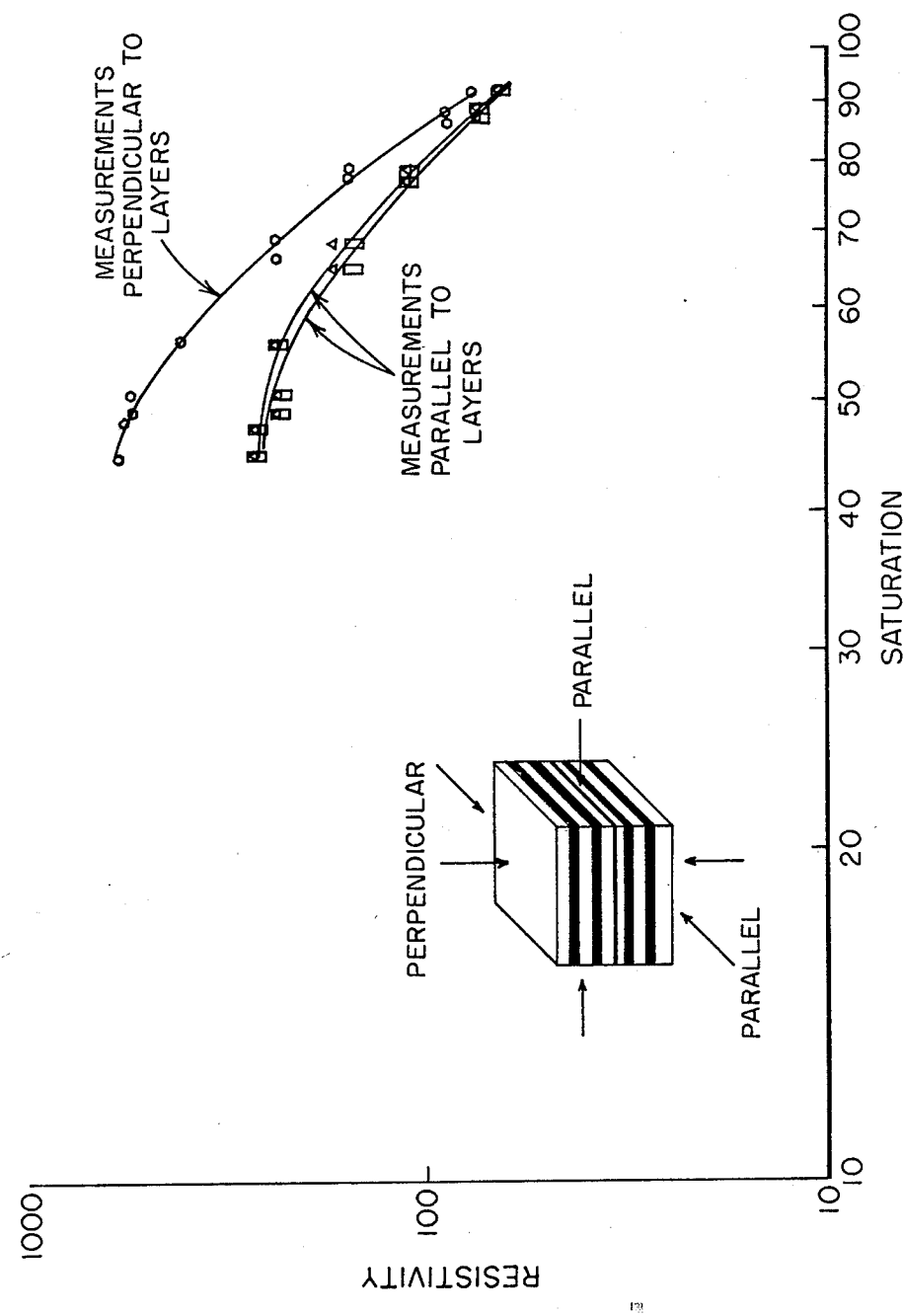
FIG. 4 is a logarithmic plot of resistivity versus saturation of measurements obtained parallel and perpendicular to contrasting layers of a cube sample.

After completion of the resistivity measurements, a logarithmic plot is made of resistivity versus fluid saturation for each of the mutually perpendicular azimuthal directions so that any electrical anisotropy with direction can be identified as described above from divergence of the plots for the different directions with decreasing conducting fluid saturation (FIG. 4).

Figure 3:
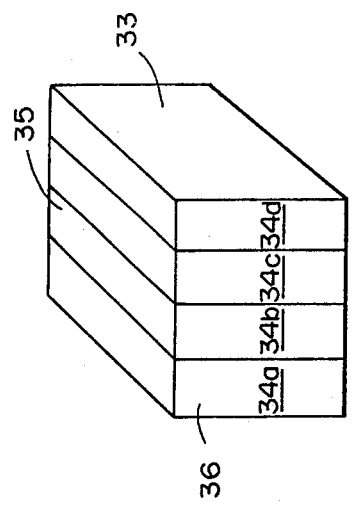
FIG. 3 illustrates the orientation of laminations or permeability barriers within a core sample shaped with a plurality of pairs of parallel planar outer surfaces in accordance with the present invention.

In a further aspect of the invention, it may be preferable to shape the core sample into a cube having one pair of parallel, planar outer surfaces, such as 33 in FIG. 3, parallel to any core sample laminations 34a through 34d and having two pairs of parallel, planar outer surfaces 35 and 36 perpendicular t such laminations.

Having now described a preferred embodiment of apparatus for use in carrying out the method of the present invention, it is to be understood that various modifications or changes may be made without departing from the spirit and scope of the present invention as set forth in the appended claims.

We claim:

1. A method for measuring electrical anisotropy of a core sample from a subterranean formation, comprising the steps of:
   (a) shaping said core sample to provide a plurality of pairs of parallel, planar outer surfaces on said core sample,
   (b) measuring electrical resistivity in each of the azimuthal directions through said core sample which are perpendicular to each of said pairs of parallel, planar outer surfaces for each of a plurality of differing fluid saturations within said core sample, and
   (c) comparing each of said measured electrical resistivities to identify the azimuthal direction of any electrical anisotropy through said core sample.

2. The method of claim 1 wherein the step of comparing said measured electrical resistivities comprises the steps of:
   (a) plotting a logarithm of resistivity versus a logarithm of water saturation for each azimuthal direction through said core sample perpendicular to said pairs of parallel, planar outer surfaces,
   (b) identifying an electrical isotropic condition within said core sample for each of said azimuthal directions for which the plotting of the logarithm of resistivity versus the logarithm of fluid saturation results in the same plot for all directions, and
   (c) identifying an electrical anisotropic condition within said core sample for each of said azimuthal directions for which the plotting of the logarithm of resistivity versus the logarithm of fluid saturation results in different plots for at least 2 different directions.

3. The method of claim 1 wherein the step of measuring electrical resistivity comprising the steps of:
   (a) establishing an initial fluid saturation within said core sample,
   (b) measuring electrical resistivity in each of the azimuthal directions through said core sample which are perpendicular to each of said pairs of parallel, planar outer surfaces at said initial fluid saturation,
   (c) altering said fluid saturation within said core sample a plurality of times and repeating the electrical resistivity measurements for each differing fluid saturation.

4. The method of claim 3 wherein the step of measuring electrical resistivity is carried out sequentially in each of said azimuthal directions for each differing fluid saturation.

5. The method of claim 4 wherein the step of measuring electrical resistivity comprises the steps of:
   (a) initially contacting a first of said pairs of parallel, planar outer surfaces with a pair of resistivity measuring electrodes,
   (b) measuring electrical resistivity through said core sample between said pair of electrodes at said initial fluid saturation, and
   (c) sequentially placing said pair of electrodes into contact with each of the remaining pairs of parallel, planar outer surfaces and measuring electrical resistivity through said core sample at each placement of said electrodes for said initial fluid saturation.

6. The method of claim 5 wherein said pair of electrodes initially contact the entire outer surfaces of said first of said pairs of parallel, planar outer surfaces and thereafter sequentially contact the entire outer surfaces of said remaining pairs of parallel, planar outer surfaces.

7. The method of claim 3 wherein the step of altering fluid saturation uniformly desaturates said core sample on opposite sides of any permeability barrier within said core sample.

8. The method of claim 3 wherein the step of altering fluid saturation comprises the step of minimizing fluid flow across any permeability barrier within said core sample.

9. The method of claim 8 wherein the step of altering fluid saturation comprises the step of moving the fluid in the core sample in a direction parallel to any said permeability barrier.

10. The method of claim 1 wherein the step of shaping said core sample is carried out to provide first, second and third pairs of parallel, planar outer surfaces which are mutually perpendicular to one another.

11. The method of claim 10 wherein the step of shaping said core sample is carried out to provide a cube.

12. The method of claim 1 wherein the step of shaping said core sample is carried out to provide at least one pair of parallel, planar outer surfaces which are perpendicular to any permeability barriers or laminations within said core sample.

13. The method of claim 1 wherein the step of shaping said core sample is carried out to provide at least one pair of parallel planar outer surfaces which are parallel to any permeability barriers or laminations within said core sample.

14. The method of claim 1 wherein the step of shaping said core sample is carried out to provide at least one pair of parallel, planar outer surfaces which are parallel to any permeability barriers or laminations within said core sample and at least one pair of parallel, planar outer surfaces which are perpendicular to any permeability barriers or laminations within said core sample.

15. The method of claim 14 wherein the step of shaping said core sample is carried out to provide a first pair of parallel, planar outer surfaces which are parallel to any permeability barriers or laminations within said core sample and second and third pairs of parallel, planar outer surfaces which are perpendicular to any permeability barriers within said core sample, each of said first, second and third pairs being mutually perpendicular to one other.

16. The method of claim 15 wherein the step of shaping said core sample is carried out to form a cube.

* * * * *